United States Patent [19]

Spivack et al.

[11] 4,456,716
[45] Jun. 26, 1984

[54] 4-(HYDROXYPHENYLTHIO)IMIDE STABILIZERS

[75] Inventors: John D. Spivack; Stephen D. Pastor, both of Spring Valley, N.Y.

[73] Assignee: Ciba-Geigy Corporation, Ardsley, N.Y.

[21] Appl. No.: 454,214

[22] Filed: Dec. 29, 1982

[51] Int. Cl.$^3$ .................. C07D 207/416; C08K 5/36
[52] U.S. Cl. ..........................:........... 524/104; 524/105; 548/545; 548/547
[58] Field of Search ............ 524/100, 104, 105; 544/198, 209, 212; 548/520, 545, 547

[56] References Cited

U.S. PATENT DOCUMENTS

| | | | |
|---|---|---|---|
| 3,255,191 | 6/1966 | Dexter et al. | 524/100 |
| 3,625,978 | 12/1971 | Geering et al. | 548/547 |
| 3,763,090 | 10/1973 | Cyba | 524/100 |
| 3,790,597 | 2/1974 | Dexter et al. | 524/105 |
| 3,887,516 | 6/1975 | Song | 524/100 |
| 4,226,989 | 10/1980 | DiLeone et al. | 524/94 |

*Primary Examiner*—John Kight, III
*Assistant Examiner*—R. A. White
*Attorney, Agent, or Firm*—Harry Falber

[57] ABSTRACT

(4-Hydroxyphenylthio)imide stabilizers of the formula

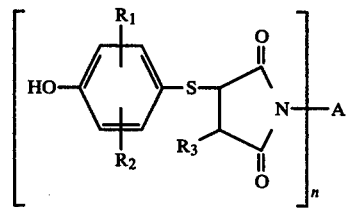

are prepared by the reaction of the appropriate maleimide and mercaptophenol compounds, said imides being useful as stabilizers of organic polymers.

17 Claims, No Drawings

4-(HYDROXYPHENYLTHIO)IMIDE STABILIZERS

Organic polymeric materials such as plastics and resins, are subject to thermal, oxidative and photo-degradation. A great variety of stabilizers are known in the art for stabilizing a diversity of substrates. Their effectiveness varies depending upon the causes of degradation and the substrate stabilized. In general, it is difficult to predict which stabilizer will be most effective and most economical for any one area of application. For example, stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

It has now been determined that the (hydroxyphenylthio)imide derivatives of this invention possess an unusual combination of desirable properties which makes them particularly effective and useful as stabilizers. The compounds are particularly effective in protecting high impact polystyrene, rubbers such as polybutadiene and styrene-butadiene rubber, and other elastomers wherein retention of elasticity and inhibition of crosslinking, crazing, discoloration, odor formation and exudation are basic requirements.

It is the primary object of this invention to provide a class of mercaptophenol derivatives which exhibit a broad range of improved stabilization performance characteristics.

Various other objects and advantages of this invention will become evident from the following description thereof.

The compounds of this invention correspond to the formula

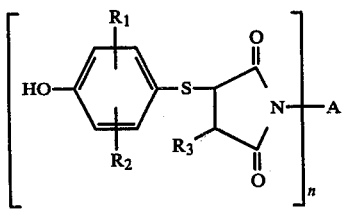

wherein $R_1$ and $R_2$ independently are hydrogen, alkyl of 1 to 18 carbon atoms, cycloalkyl of 5 to 6 carbon atoms, phenyl or phenyl substituted by alkyl of 1 to 12 carbon atoms;

$R_3$ is hydrogen or alkyl of 1 to 3 carbon atoms;

n is 1, 2 or 3;

when n is 1, A is hydrogen, phenyl, phenyl substituted by one or two alkyl groups of 1 to 18 carbon atoms, alkyl of 1 to 30 carbon atoms, cycloalkyl of 5 to 6 carbon atoms; or is E—(G-T)$_y$— where E is alkyl of 1 to 18 carbon atoms, G is —O— or —NH—, T is ethylene, propylene or 1,4-butylene and y is 1 to 30, or is the group

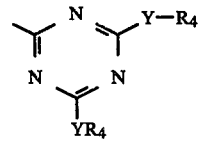

where

Y is —O—, —S— or —NR$_5$— where $R_4$ and $R_5$ are independently of one another alkyl of 1 to 18 carbon atoms, phenyl or phenyl substituted by one or two alkyl groups of 1 to 18 carbon atoms;

when n is 2, A is phenylene, phenylene substituted by one or two alkyl groups of 1 to 12 carbon atoms, alkylene of 1 to 12 carbon atoms, cycloalkylene of 5 to 6 carbon atoms, phenylene-L-phenylene where L is alkylene of 1 to 4 carbon atoms, or is —T—(G-T)$_z$— where T is ethylene, propylene or 1,4-butylene, G is —O— or —NH—, and z is 1 to 30, or is a group

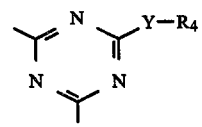

where

Y and $R_4$ are defined as above; and when n is 3, A is 1,2,3-benzenetriyl, 1,2,4-benzenetriyl, 1,3,5-benzenetriyl, N(—$R_6$—)$_3$ where $R_6$ is alkylene of 2 to 4 carbon atoms, or is the group

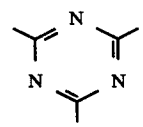

Preferred compounds within the above structure are those wherein $R_1$ is in the ortho position to the hydroxyl group in the phenyl ring.

The $R_1$ and $R_2$ groups are preferably straight-chain or branched alkyl with 4 to 8 carbon atoms, such as n-butyl, sec-butyl, tert-butyl, tert-pentyl, 2-ethylhexyl, n-octyl and tert-octyl. The groups tert-butyl, tert-pentyl and tert-octyl are especially preferred. Also especially preferred is for the $R_2$ group to be in the ortho position to the hydroxy group, particularly if $R_2$ is tert-alkyl.

The substituents on the phenyl in $R_1$ and $R_2$ are alkyl of 1 to 12 carbon atoms, and preferably 1 to 8 carbon atoms.

When n is 1, A is preferably phenyl or alkyl of 1 to 12 carbon atoms; when n is 2, A is preferably hexamethylene, phenylene or 4,4'-methylenediphenylene; and, when n is 3, A is preferably 1,3,5-benzenetriyl or N(CH$_2$CH$_2$—)$_3$.

The imides of this invention can be prepared by reacting the appropriately substituted maleimide with an alkylated mercaptophenol, optionally in a solvent, to yield the desired product. The solvent can be an aromatic hydrocarbon such as benzene, toluene, xylene, and the like, or a heterocyclic ether, such as tetrahydrofuran. The reaction temperature ranges from room temperature to 70° C. The preferred method for preparing the compounds of this invention involves reacting the maleimide with the mercaptophenol in the presence of a proton acceptor such as a tertiary amine, for example, triethylamine or pyridine.

The starting materials needed to prepare these imides are items of commerce or can be prepared by known methods. For example, the substituted maleimides can be prepared by reacting ammonia or primary amines with a cyclic anhydride such as maleic or citraconic anhydride. A review of such preparative methods for making cyclic imides is seen in Hargreaves, Pritchard and Dave, Chemical Reviews, Vol. 70, 439–469 (1970). Typical maleimides, where $R_3$ is hydrogen, include N,N-hexamethylene bis-(maleimide), N-phenylmaleimide, N-methylmaleimide, 1,4-bis(maleimido)benzene, N-n-butylmaleimide, N,N-o-phenylene dimaleimide, N-dodecylmaleimide, 4,4'-bis(maleimido)-diphenylmethane and N-cyclohexylmaleimide. Similar citraconimides, where $R_3$ is methyl, are also useful in this invention.

The mercaptophenols correspond to the formula

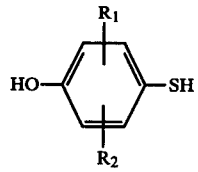

wherein $R_1$ and $R_2$ are as previously defined. Preferred 4-mercaptophenols include 2,6-di-tert.butyl- and 2-tert.butyl-6-methyl-4-mercaptophenol as well as 2,6-dimethyl-4-mercaptophenol and 2-tert-butyl-5-methylphenol.

Compounds of this invention are effective in stabilizing organic materials such as plastics, polymers and resins.

The compounds of the invention are particularly useful as stabilizers, especially for the protection of polyolefins, for instance, polyethylene, polypropylene, polyisobutylene, poly(butene-1), poly(pentene-1), poly(3-methylbutene-1), poly(4-methyl-pentene-1), various ethylene-propylene copolymers and the like; polystyrene, including impact polystyrene, ABS resin, SBR, polyisoprene, as well as natural rubber, polyesters including polyethylene terephthalate and polybutylene terephthalate, including copolymers.

Polyurethanes, polycarbonates, polyamides such as nylon 6, 6/6 and the like as well as copolyamides and polysulfones are also stabilized.

In general, polymers which can be stabilized include:
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.
2. Mixtures of the polymers mentioned under (1), for example mixtures of polypropylene with polyethylene or with polyisobutylene.
3. Copolymer of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/ethyl acrylate, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene norbornene.
4. Polystyrene.
5. Random copolymers of styrene of α-methylstyrene with dienes or acrylic derivatives, such as, for example, styrene/butadiene, styrene/acrylonitrile, styrene/alkyl methacrylates, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.
6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS—, MBS—, ASA— or AES-polymers.
7. Halogen-containing polymers, such as polychloroprene, chlorinated rubbers, chlorinated or sulfochlorinated polyethylene, polymers from halogen-containing vinyl compounds, as for example, polyvinyl chloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.
8. Polymers which are derived from α,β-unsaturated acids and derivatives thereof, such as polyacrylates and polymethacrylates, polyacrylamides and polyacrylonitrile.
9. Copolymers from the monomers mentioned under (8) with each other or with other unsaturated monomers, such as, for instance, acrylonitrile/butadiene, acrylonitrile/alkyl acrylate or acrylonitrile/vinyl chloride copolymers or acrylonitrile/alkyl methacrylate/butadiene terpolymers.
10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallylmelamine.
11. Homopolymers and copolymers of cyclic ethers, such as polyalkylene glycols, polyethylene oxide, polypropylene oxide or copolymers thereof with bis-glycidyl ethers.
12. Polyacetals, such as polyoxymethylene and those polyoxymethylenes which contain ethylene oxide as a comonomer.
13. Polyphenylene oxides and sulfides.
14. Polyurethanes which are derived from polyethers, polyesters or polybutadienes with terminal hydroxyl groups on the one side and aliphatic or aromatic polyisocyanates on the other side, as well as precursors thereof.
15. Polyamides and copolyamides which are derived from diamines and dicarboxylic acids and/or from aminocarboxylic acids of the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance, with polyethylene glycol, polypropylene glycol or polytetramethylene glycols.

16. Polyureas, polyimides and polyamide-imides.
17. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate and polyhydroxybenzoates as well as block copolyetheresters derived from polyethers having hydroxyl end groups.
18. Polycarbonates.
19. Polysulfones and polyethersulfones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyd resins.
22. Unsaturated polyester resins which are derived from copolyesters of saturated and unsaturated dicarboxylic acids with polyhydric alcohols and vinyl compounds as crosslinking agents, and also halogen-containing modifications thereof of low flammability.
23. Thermosetting acrylic resins, derived from substituted acrylic esters, such as epoxy-acrylates, urethaneacrylates or polyester-acrylates.
24. Alkyd resins, polyester resins or acrylate resins in admixture with melamine resins, urea resins, polyisocyanates or epoxide resins as crosslinking agents.
25. Crosslinked epoxide resins which are derived from polyepoxides, for example from bis-glycidyl ethers or from cycloaliphatic diepoxides and aromatic diepoxides.
26. Natural polymers, such as cellulose, rubber, gelatin and derivatives thereof which are chemically modified in a polymer-homologous manner, such as cellulose acetates, cellulose propionates and cellulose butyrates, or the cellulose ethers, such as methylcellulose.
27. Naturally occurring and synthetic organic materials which are pure monomeric compounds or mixtures of such compounds, for example mineral oils, animal and vegetable fats, oils and waxes, or oils, fats and waxes based on synthtic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.
28. Aqueous emulsions of natural or synthetic rubber, e.g. natural latex or latices of carboxylated styrene/butadiene copolymers.

In general, the stabilizers of this invention are employed in from about 0.01 to about 5% by weight of the stabilized composition, although this will vary with the particular substrate and application. An advantageous range is from about 0.05 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following:

1. Antioxidants
1.1 Simple 2.6-dialkylphenols, such as, for example, 2,6-di-tert.-butyl-4-methylphenol, 2-tert.-butyl-4,6-dimethylphenol, 2,6-di-tert.-butyl-4-methoxymethylphenol and 2,6-di-octadecyl-4-methylphenol.
1.2. Derivatives of alkylated hydroquinones, such as, for example, 2,5-di-tert.-butyl-hydroquinone, 2,5-di-tert.-amyl-hydroquinone, 2,6-di-tert.-butyl-hydroquinone, 2,6-di-tert.-butyl-4-hydroxy-anisole, 3,5-di-tert.-butyl-4-hydroxy-anisole, tris-(3,5-di-tert.-butyl-4-hydroxyphenyl) phosphite, 3,5-di-tert.-butyl-4-hydroxyphenyl stearate and bis-(3,5-di-tert.-butyl-4-hydroxyphenyl) adipate.
1.3. Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxy-phenyl) disulphide.
1.4. Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6-di-tert.-butyl-phenol), 2,6-di-(3-tert.-butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercaptobutane, 1,1,5,5-tetra-(5-tert.-butyl-4-hydroxy-2-methylphenyl)-pentane and ethylene glycol bis-[3,3-bis-(3'-tert.-butyl-4'-hydroxyphenyl)-butyrate].
1.5. O-, N- and S-benzyl compounds, such as, for example, 3,3', 5,5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.-butyl-3-hydroxy-2,6-dimethylbenzyl) dithioterephthalate.
1.6. Hydroxybenzylated malonates, such as, for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)-phenyl] 2,2-bis-(3,5-di-tert.-butyl-4-hydroxybenzyl)-malonate. butyl-phenol), 2,6-di-(3-tert.-butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercaptobutane, 1,1,5,5-tetra-(5-tert.-butyl-4-hydroxy-2-methylphenyl)-pentane and ethylene glycol bis-[3,3-bis-(3'-tert.-butyl-4'-hydroxyphenyl)-butyrate].
1.5. O-, N- and S-benzyl compounds, such as, for example, 3,3', 5,5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.-butyl-3-hydroxy-2,6-dimethylbenzyl) dithioterephthalate.

1.6. Hydroxybenzylated malonates, such as, for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)-phenyl] 2,2-bis-(3,5-di-tert.-butyl-4-hydroxybenzyl)-malonate.

1.7. Hydroxybenzyl-aromatic compounds, such as, for example, 1,3,5-tris-(3,5-di-tert.-butyl-4-hydroxybenzyl)-2,4,6-trimethylbenzene, 1,4-bis-(3,5-di-tert.-butyl-4-hydroxybenzyl)-2,3,5,6-tetramethylbenzene and 2,4,6-tri-(3,5-di-tert.-butyl-4-hydroxybenzyl)-phenol.

1.8. s-Triazine compounds, such as, for example, 2,4-bisoctylmercapto-6-(3,5-di-tert.-butyl-4-hydroxyanilino)-s-triazine, 2-octylmercapto-4,6-bis-(3,5-di-tert.-butyl-4-hydroxyanilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert.-butyl-4-hydroxyphenylethyl)-s-triazine and 1,3,5-tris-(3,5-di-tert.-butyl-4-hydroxybenzyl)isocyanurate.

9. Amides of β-(3,5-di-tert.-butyl-4-hydroxyphenyl) propionic acid, such as, for example, 1,3,5-tris-3,5-di-tert.-butyl-4-hydroxyphenyl-propionyl)-hexahydro-s-triazine and N,N′-di-(3,5-di-tert.-butyl-4-hydroxyphenyl-propionyl)-hexamethylenediamine. N,N′-bis-β-(3,5-di-t-butyl-4-hydroxyphenyl-propionyl)-hydrazine.

1.10. Esters of β-(3,5-di-tert.-butyl-4-hydroxyphenyl) propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, triethylene glycol, thiodiethylene glycol, neopentylglycol, pentaerythritol, 3-thia-undecanol, 3-thiapentadecanol, trimethylhexanediol, trimethylolethane, trimethylolpropane, tris-hydroxyethyl isocyanurate and 4-hydroxy-methyl-1-phospha-2,6,7-trioxabicyclo-[2,2,2]octane.

1.11. Esters of β(5-tert.-butyl-4-hydroxy-3-methylphenyl)-propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, triethylene glycol, thiodiethylene glycol, neopentylglycol, pentaerythritol, 3-thia-undecanol, 3-thiapentadecanol, trimethylhexanediol trimethylolethane, trimethylolpropane, tris-hydroxyethyl isocyanurate and 4-hydroxymethyl-1-phospha-2,6,7-trioxabicyclo [2,2,2]octane.

1.12. Esters of 3,5-di-tert.-butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiglycol, neopentylglycol, pentaerythritol, 3-thia-undecanol, 3-thiapentadecanol, trimethylhexanediol, trimethylolethane, trimethylolpropane, tris-hydroxyethyl isocyanurate and 4-hydroxymethyl-1-phospha-2,6,7-trioxabicyclo [2,2,2]-octane, especially the tetra-bis ester of pentaerythritol.

1.13. Benzylphosphonates, such as, for example, dimethyl 3,5-di-tert.-butyl-4-hydroxybenzyl-phosphonate, diethyl 3,5-di-tert.butyl-4-hydroxybenzyl-phosphonate, dioctadecyl 3,5-di-tert. butyl-4-hydroxybenzyl-phosphonate and dioctadecyl 5-tert.-butyl-4-hydroxy-3-methylbenzyl-phosphonate.

The following may be mentioned as examples of further additives that can be used together with the stabilizer of this invention and the antioxidant:

1. Aminoaryl derivatives, e.g. phenyl-1-naphthylamine, phenyl-2-naphthylamine, N,N′-di-phenyl-p-phenylenediamine, N,N′-di-2-naphthyl-p-phenylenediamine, N,N′-di-naphthyl-p-phenylenediamine, N,N′-di-sec.-butyl-p-phenylenediamine, 6-ethoxy-2,2,4-trimethyl-1,2-dihydroquinoline, 6-dodecyl-2,2,4-trimethyl-1,2-dihydroquinoline, mono- and dioctyliminodibenzyl, polymerized 2,2,4-trimethyl-1,2,-dihydroquinoline.

Octylated diphenylamine, nonylated diphenylamine, N-phenyl-N′-cyclohexyl-p-phenylenediamine, N-phenyl-N′-isopropyl-p-phenylenediamine, N,N′-di-sec.octyl-p-phenylenediamine, N-phenyl-N′-sec.-octyl-p-phenylenediamine, N,N′-di-(1,4-dimethylpentyl)-p-phenylenediamine, N,N′-dimethyl-N,N′-di-(sec.-octyl)-p-phenylenediamine, 2,6-dimethyl-4-methoxyaniline, 4-ethoxy-N-sec.-butylaniline, diphenylamineacetone condensation product, aldol-1-naphthylamine and phenothiazine.

Discoloration effects have to be taken into account when using the above antioxidants.

2. UV-Absorbers and light-stabilising agents 2.1. 2-(2′-Hydroxyphenyl)-benzotriazoles, e.g. the 5′-methyl-, 3′,5′-di-tert.-butyl-, 5′-tert.butyl-, 5′-(1,1,3,3-tetramethylbutyl)-, 5-chloro-3′,5′-di-tert.-butyl-, 5-chloro-3′-tert.-butyl-5′-methyl-, 3′-sec.-butyl-5′-tert.-butyl-, 3′-alpha-methylbenzyl-5′-methyl-, 3′-alpha-methylbenzyl-5′-methyl-5-chloro-, 4′-hydroxy-, 4′-methoxy-, 4′-octoxy-, 3′,5′-di-tert.-amyl-, 3′-methyl-5′-carbomethoxyethyl-, 3′,5′-bis(alpha,alpha-dimethylbenzyl),3′,5′-bis(alpha,alpha-dimethyl benzyl)-5-chloro-, 3′,5′-di-tert.-octylphenyl, 3′,5′-di-tert.-octylphenyl-5-chloro- and 5-chloro-3′,5′-di-tert.-amyl-derivatives.

2.2. 2,4-bis-(2′-Hydroxyphenyl)-6-alkyl-s-triazines, e.g. the 6-ethyl-, 6-heptadecyl- or 6-undecyl-derivative.

2.3. 2-Hydroxybenzophenones, e.g. the 4-hydroxy-, 4-methoxy-, 4-octoxy-, 4-decyloxy-, 4-dodecyloxy-, 4-benzyloxy-, 2′,4-4′-trihydroxy- or 2′-hydroxy-4,4′-dimethoxy-derivative.

2.4. 1,3-bis-(2′-Hydroxybenzoyl)-benzenes, e.g. 1,3-bis-(2′-hydroxy-4′-hexyloxy-benzoyl)-benzene, 1,3-bis-(2′-hydroxy-4′-octyloxy-benzoyl)-benzene or 1,3-bis-(2′-hydroxy-4′dodecyloxy-benzoyl)-benzene.

2.5. Esters of optionally substituted benzoic acids, e.g. phenylsalicylate, octylphenylsalicylate, dibenzoylresorcin, bis-(4-tert.-butylbenzoyl)-resorcin, benzoylresorcin, 3,5-di-tert.-butyl-4-hydroxybenzoic acid-2,4-di-tert.-butylphenyl ester or -octadecyl ester or n-hexadecyl ester or -2-methyl-4,-6-di-tert.-butyl ester.

2.6. Acrylates, e.g. α-cyano-β,β-diphenylacrylic acid-ethyl ester or -isooctyl ester, α-carbomethoxy-cinnamic acid methyl ester, α-cyano-β-methyl-p-methoxy-cinnamic acid methyl ester or butyl ester of N-(β-carbomethoxyvinyl)-2-methyl-indoline.

2.7. Sterically hindered amines, e.g. 4-benzoyl-2,2,6,6-tetramethylpiperidine, 4-stearyl-oxy-2,2,6,6-tetramethylpiperidine, bis-(2,2,6,6-tetramethylpiperidyl)- sebacate or 3-n-octyl-7,7,9,9-tetramethyl-1,3,8-triazaspiro[4,5]decane-2,4-dione.

2.8. Oxalic acid diamides, e.g. 4,4'-di-octyloxy-oxanilide, 2,2'-di-dodecyloxy-5,5'-di-tert.-butyl-oxanilide, 2-ethoxy-2'-ethyl-oxanilide, N,N'-bis-(3-dimethylaminopropyl)-oxalamide, 2-ethoxy-5-tert.-butyl-2'-ethyl-5,4'-di-tert.-butyl-oxanilide, or mixtures of ortho- and para-methoxy- as well as of o- and p-ethoxy-disubstituted oxanilides.

3. Metal deactivators, e.g. oxanilide, isophthalic acid dihydrazide, sebacic acid-bis-phenylhydrazide, bis-benzylidene-oxalic acid dihydrazide, N,N'-diacetyladipic acid dihydrazide, N,N'-bis-salicyloyloxalic acid dihydrazide, N,N'-bis-salicyloylhydrazine, N,N'-bis-(3,5-di-tert.-butyl-4-hydroxyphenylpropionyl)-hydrazine, N-salicyloyl-N'-salicylalhydrazine, 3-salicyloyl-amino-1,2,4-triazole or N,N'-bis-salicyloyl-thiopropionic acid dihydrazide.

4. Basic co-stabilisers, e.g. alkali metal salts and alkaline-earth metal salts of higher fatty acids, for example Ca-stearate, Zn-stearate, Mg-behenate, Na-ricinoleate or K-plamitate.

5. Nucleation agents, e.g. 4-tert.-butylbenzoic acid, adipic acid or diphenylacetic acid.

6. Phosphites, such as, for example, triphenyl phosphite, diphenylalkyl phosphites, phenyldialkyl phosphites, tri-(nonylphenyl) phosphite, trilauryl phosphite, trioctadecyl phosphite, 3,9-isodecyloxy-2,4,8,10-tetraoxa-3,9-diphospha spiro [5, 5]-undecane and tri-(4-hydroxy-3,5-di-tert.butylphenyl) phosphite.

Other additives that can be incorporated in the stabilized compositions are thiosynergists such as dilaurylthiodipropionate or distearylthiodipropionate, lubricants such as stearyl alcohol fillers, carbon black, asbestos, kaolin, talc, glass fibers, pigments, optical brighteners, flameproofing agents and antistatic agents.

The compounds of this invention may be used alone as the sole stabilizer having either mainly an antioxidant function or a light stabilizing function or the stabilizer may combine utility as an antioxidant and light stabilizer. The stabilizers may be used with phenolic antioxidants, lubricants such as calcium stearate, pigments, colorants or dyes, UV absorbers, light stabilizers such as hindered amines, metal deactivators, talc and other fillers, etc.

The following examples further illustrate the embodiments of this invention. In these examples, all parts given are by weight unless otherwise specified.

EXAMPLE 1

N,N'-Hexamethylene bis[2-(3,5-di-tert-butyl-4-hydroxyphenylthio)succinimide]

A solution of 11.05 grams N,N'-hexamethylene bis(maleimide) in 50 ml of tetrahydrofuran is charged into a flask under nitrogen and is treated slowly with a solution of 19.07 grams of 2,6-di-tert-butyl-4-mercaptophenol and 0.4 grams of triethylamine in 100 ml of toluene. After stirring for three hours, the solvent is removed in vacuo and the residue is recrystallized from cyclohexane to give 16.64 grams (58% yield) of off-white solid, mp 69°–72° C.

Anal. Calcd. for $C_{42}H_{60}N_2O_6S_2$: C, 67.0; H, 8.0; N, 3.7. Found: C, 67.4; H, 8.2; N, 3.6.

EXAMPLE 2

N-Phenyl-2-(3,5-di-tert-butyl-4-hydroxyphenylthio)-succinimide

The procedure of Example 1 is repeated using 10 grams of 2,6-di-tert-butyl-4-mercaptophenol, 7.26 grams of N-phenyl maleimide, and 0.73 grams of triethylamine. The residue is recrystallized from isopropanol to give 2.3 grams (48% yield) of white solid, m.p. 134°–137° C.

Anal. Calcd. for $C_{24}H_{29}NO_3S$: C, 70.0; H, 7.1; N, 3.4; S, 7.8. Found: C 69.8; H, 6.8; N, 3.4; S, 7.9.

EXAMPLE 3

N-Phenyl-2-(3-tert-butyl-5-methyl-4-hydroxyphenylthio)-succinimide

The procedure of Example 1 is repeated using 9.82 grams of 2-tert-butyl-6-methyl-4-mercaptophenol, 8.66 grams of N-phenylmaleimide, and 0.5 grams of triethylamine. The residue is recrystallized from a heptane-toluene mixture to give 16.44 grams of a white solid, m.p. 158°–160° C.

Anal. Calcd. for $C_{21}H_{23}NO_3S$: C, 68.3; H, 6.3; N, 3.8. Found: C, 68.5; H, 6.3; N, 3.7.

EXAMPLE 4

N-Methyl-2-(3,5-di-tert-butyl-4-hydroxyphenylthio)-succinimide

The procedure of Example 1 is repeated using 11.92 grams 2,6-di-tert-butyl-4-mercaptophenol, 5.55 grams N-methylmaleimide, and 0.5 grams triethylamine. The residue is recrystallized from toluene: heptane to give 15.47 grams (88% yield), m.p. 132°–132.5° C.

Anal. Calcd. for $C_{19}H_{27}NO_3S$: C, 65.3; H, 7.8; N, 4.0. Found: C, 65.1; H, 7.6; N, 4.4.

EXAMPLE 5

1,4-Bis[2-(3,5-di-tert-butyl-4-hydroxyphenylthio)succinimido]-benzene

The procedure of Example 1 is repeated using 17.8 grams of 2,6-di-tert-butyl-4-mercaptophenol, 10 grams of 1,4-bis(maleimido)benzene, and 0.75 grams of triethylamine. The residue is recrystallized from acetone to give 21 grams of an off-white solid, m.p. 274°–278° C.

Anal. Calcd. for $C_{42}H_{52}N_2O_6S_2$: C, 67.7; H, 7.0; N, 3.8; S, 8.6. Found: C, 67.8; H, 7.3; N, 3.7; S, 8.6.

EXAMPLE 6

N-n-Butyl-2-(3,5-di-tert-butyl-4-hydroxyphenylthio)-succinimide

The procedure of Example 1 is repeated using 11.92 grams 2,6-di-tert-butyl-4-mercaptophenol, 7.66 grams N-n-butyl-maleimide, and 0.5 grams triethylamine. The residue is purified by dry column chromatography to give a white solid, m.p. 80°–85° C.

Anal. Calcd. for $C_{22}H_{33}NO_3S$: S, 8.2. Found: S, 8.2.

EXAMPLE 7

1,2-Bis[2-(3,5-di-tert-butyl-4-hydroxyphenylthio)succinimido]-benzene

The procedure of Example 1 is repeated using 11.92 grams 2,6-di-tert-butyl-4-mercaptophenol, 6.71 grams N,N-o-phenylenedimaleimide, and 0.5 grams triethylamine. The residue is recrystallized twice from heptane:

toluene to give 7.9 grams of a white solid, m.p. 128°–133° C.

Anal. Calcd. for $C_{42}H_{52}N_2O_6S_2$: C, 67.7; H, 7.0; N, 3.8. Found: C, 67.5; H, 6.9; N, 3.7.

EXAMPLE 8

N-Dodecyl-2-(3,5-di-tert-butyl-4-hydroxyphenylthio)-succinimide

The procedure of Example 1 is repeated using 13.27 grams N-dodecylmaleimide, 11.92 grams 2,6-di-tert-butyl-4-mercaptophenol, and 0.5 grams triethylamine. The sample is purified by dry column chromatography to give 10.0 grams of a clear syrup.

Anal. Calcd. for $C_{30}H_{49}NO_3S$: C, 71.5; H, 9.8; N, 2.8. Found: C, 71.3; H, 9.8; N, 2.9.

EXAMPLE 9

4,4′-Bis[2-(3,5-di-tert-butyl-4-hydroxyphenylthio)-succinimido]-diphenylmethane The procedure of Example 1 is repeated using 9.17 grams 4,4′-bis(maleimido)-diphenylmethane, 12.20 grams 2,6-di-tert-butyl-4-mercaptophenol, and 0.5 grams triethylamine. The residue is purified by dry column chromatography to give 1.3 grams of a white solid, m.p. 103°–110° C.

Anal. Calcd. for $C_{49}H_{58}N_2O_6S_2$: C, 70.5; H, 7.0; N, 3.4. Found: C, 70.8; H, 6.9; N, 3.1.

EXAMPLE 10

N-Cyclohexyl-2-(3,5-di-tert-butyl-4-hydroxyphenylthio)-succinimide

The procedure of Example 1 is repeated using 11.95 grams of 2,6-di-tert-butyl-4-mercaptophenol, 8.96 grams of N-cyclohexylmaleimide, and 0.5 grams of triethylamine. The residue is recrystallized from a heptane-toluene mixture to give 10.5 grams of a white solid, m.p. 94°–98° C.

Anal. Calcd. for $C_{24}H_{35}NO_3S$: C, 69.0; H, 8.5; N, 3.4; S, 7.7. Found: C, 69.0; H, 8.3; N, 3.4; S, 7.7.

EXAMPLE 11

This example illustrates the stabilizing effectiveness of the instant stabilizer in impact polystyrene.

In the laboratory procedure utilized herein, a solution of eight (8) weight percent polybutadiene rubber (Firestone-DIENE 55) dissolved in styrene monomer is prepared on a roller mill. The indicated amount of stabilizer is also introduced at this point. 500 ppm of zinc stearate are added to aid in removing the sample from the bottle after the polymerization. The bottle is screwed into the polymerization apparatus which is equipped with a double helical ribbon stirrer. Since most commercial IPS bulk polymerizations are thermally initiated processes, no initiator is used in the laboratory process. A nitrogen atmosphere is established and the reactor is then heated to 121° C. within ½ hour. Heating continues at 121° C. with efficient stirring until there is a 30 to 35% monomer conversion (2.5 hours). The stirring rate is controlled to yield a two to four μm rubber particle size. The bottles are removed from the polymerization apparatus, blanketed with nitrogen, capped, and then placed in a fluidized bed sand bath to complete the polymerization. The bottles are heated in the bath in the following fashion: one hour at 100° C. to equilibrate the temperature, one hour to reach 140° C. and then an additional eight hours with the temperature increasing at the rate of 10° C. per hour to a maximum of 220° C. After the resin has cooled, the bottle is broken and the glass removed. The average weight of the polymer block is slightly over 600 grams. The block is then placed into a vacuum oven at 200° C. and a vacuum of 1 mm applied as the polymer is heated for 45 minutes in order to remove all volatiles. The block is removed from the oven, immediately placed in a heated (205° C.) hydraulic press and then pressed into a thick slab between two sheets of aluminum foil (three minutes heating, five minutes in a cold press). The slab is split with a hand saw and the pieces are granulated.

All batches are extruded at 205° C. and then pelletized. The pellets are compression molded at 205° C. into 125 mil (3.175 mm) tensile bars. The bars are then aged at 150° C. on glass plates placed on rotating shelves in a forced air oven. Other tensile bars are aged at 80° C. suspended from rotating shelves in a forced air oven. The specimen yellowness index is determined on the bars at various intervals according to ASTM D-1925-63T. Correspondingly, the bars are periodically measured for percent elongation in the Instron Tensile Testing Apparatus (Instron Engineering Corporation, Massachusetts) at a pull rate of 5 mm/minute according to ASTM D-638.

| | | Oven Aged Samples @ 80° C. | | | | |
|---|---|---|---|---|---|---|
| Additive Compound of | Additive Conc. (% by weight) | % Elongation Hours at 80° C. | | | | |
| | | 0 | 300 | 600 | 900 | 1200 |
| None | — | 33 | 9 | 3 | 3 | 3 |
| Example 2 | 0.1 | 40 | 28 | 18 | 8 | 4 |
| | | Yellowness Index | | | | |
| None | — | 7 | 14 | 45 | 59 | — |
| Example 2 | 0.1 | −3 | 1 | 11 | 28 | 44 |
| | | Oven Aged Samples @ 150° C. | | | | |
| Additive Compound of | Additive Conc. (% by weight) | % Elongation Hours at 150° C. | | | | |
| | | 0 | ½ | 1 | 1½ | 2 |
| None | — | 33 | 7 | 7 | 3 | 3 |
| Example 2 | 0.1 | 40 | 42 | 14 | 13 | 10 |
| | | Yellowness Index | | | | |
| None | — | * | 18 | 30 | 38 | 43 |
| Example 2 | 0.1 | −3 | −3 | 2 | 4 | 10 |

EXAMPLE 12

Unstabilized polypropylene powder (Hercules Profax 6501) is thoroughly blended with the indicated amount of additive. The blended materials are then milled on a two roll mill at 182° C. for 5 minutes, after which time the stabilized polypropylene is sheeted from the mill and allowed to cool. The milled polypropylene is then cut into pieces and compression molded on a hydraulic press at 220° C. and 175 psi ($1.2 \times 10^6$ Pa) into 5 mil (0.127 mm) films. The sample is exposed in a fluorescent sunlight/black light chamber until failure. Failure is taken as the hours required to reach 0.5 carbonyl absorbance by infrared spectroscopy on the exposed films.

| Additive Compound of | Additive Conc. (% by weight) | FS/BL Test Results (Hours to Failure) |
|---|---|---|
| None | — | 200–300 |
| Example 1 | 0.2 | 500 |
| Example 2 | 0.2 | 400 |
| Example 6 | 0.2 | 400 |
| Example 8 | 0.2 | 380 |

| Additive Compound of | Additive Conc. (% by weight) | FS/BL Test Results (Hours to Failure) |
|---|---|---|
| Example 9 | 0.2 | 400 |

EXAMPLE 13

The oxidation stability of milled polypropylene samples from Example 12 containing 0.2% by weight of the compound of Example 1 as well as that of a synergized formulation containing 0.1% by weight of the compound of Example 1 in the presence of 0.3% by weight distearyl thiodipropionate on plaques of 25 mil (0.635 mm) thickness on exposure to air in a forced draft oven at 150° C. is measured. The plaques are considered to have failed on showing the first signs of decomposition (e.g., cracking or brown edges). Correspondingly, the color of the initial and oven aged samples is determined on the basis of the standard Gardner Color Method. (ASTM D 1544-68)

| Additive Compound of | Additive Concentration (% by weight) | Oxidative Stability Time to Failure (Hours) | Gardner Color | |
|---|---|---|---|---|
| | | | of Sample | After Hours Exposure Oven Aging |
| Base Resin (with 0.3% DSTDP*) | none | <20 | 0 | 0 |
| | | | 2 | at failure |
| Example 1 | 0.2 | 650 | 0 | 0 |
| | | | 1 | 100 |
| | | | 1 | at failure |
| Example 1 plus 0.3% DSTDP* | 0.1 | 1120 | 0 | 0 |
| | | | 1 | 100 |
| | | | 1 | at failure |

*DSTDP is distearyl thiodipropionate.

Summarizing, it is seen that this invention provides novel imide compounds which exhibit effective stabilization activity. Variations may be made in propositions, procedures and materials without departing from the scope of the invention as defined by the following claims.

What is claimed is:

1. A compound of the formula

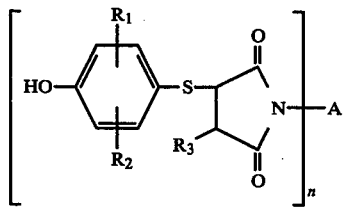

wherein $R_1$ and $R_2$ independently are hydrogen, alkyl of 1 to 18 carbon atoms, cycloalkyl of 5 to 6 carbon atoms, phenyl or phenyl substituted by alkyl of 1 to 12 carbon atoms and $R_1$ is in the ortho position to the hydroxyl group in the phenyl ring;

$R_3$ is hydrogen or alkyl of 1 to 3 carbon atoms;

n is 1, 2 or 3;

when n is 1, A is phenyl, phenyl substituted by one or two alkyl groups of 1 to 18 carbon atoms, alkyl of 1 to 30 carbon atoms, cycloalkyl of 5 to 6 carbon atoms; E-(G-T)$_y$- where E is alkyl of 1 to 18 carbon atoms, G is —O— or —NH—, T is ethylene, propylene or 1,4-butylene and y is 1 to 30;

when n is 2, A is phenylene, phenylene substituted by one or two alkyl groups of 1 to 12 carbon atoms, alkylene of 1 to 12 carbon atoms, cycloalkylene of 5 to 6 carbon atoms, phenylene-L-phenylene where L is alkylene of 1 to 4 carbon atoms, or is —T—(-G—T)$_z$— where T is ethylene, propylene or 1,4-butylene, G is —O— or —NH—, and z is 1 to 30; and when n is 3, A is 1,2,3-benzenetriyl, 1,2,4-benzenetriyl, 1,3,5-benzenetriyl or N(—R$_6$—)$_3$ where R$_6$ is alkylene of 2 to 4 carbon atoms.

2. A method for stabilizing an organic material against oxidative, thermal and actinic degradation which comprises incorporating into said organic material an effective stabilizing amount of a compound of claim 1.

3. A compound of claim 1, wherein $R_1$ is alkyl of from 4 to 8 carbon atoms.

4. A compound of claim 3, wherein $R_1$ is tert.-butyl, tert.-pentyl or tert.-octyl.

5. A compound of claim 1, wherein $R_2$ is also in the ortho position to the hydroxyl group in the phenyl ring.

6. A compound of claim 1, wherein $R_2$ is tert.-alkyl of from 4 to 8 carbon atoms.

7. A compound of claim 1, wherein n is 1 and A is phenyl or alkyl of 1 to 12 carbon atoms.

8. A compound of claim 1, wherein n is 2 and A is hexamethylene, phenylene or 4,4'-methylenediphenylene.

9. N,N'-Hexamethylene bis[2-(3,5-di-tert-butyl-4-hydroxyphenylthio)succinimide] according to claim 1.

10. N-Phenyl-2-(3,5-di-tert-butyl-4-hydroxyphenylthio)-succinimide according to claim 1.

11. N-n-Butyl-2-(3,5-di-tert-butyl-4-hydroxyphenylthio)-succinimide according to claim 1.

12. N-Dodecyl-2-(3,5-di-tert-butyl-4-hydroxyphenylthio)-succinimide according to claim 1.

13. 4,4'-Bis[2-(3,5-di-tert-butyl-4-hydroxyphenylthio)-succinimido]-diphenylmethane according to claim 1.

14. A composition of matter comprising an organic material subject to oxidative, thermal and actinic degradation stabilized with an effective stabilizing amount of a compound of claim 1.

15. A composition of claim 14, wherein the organic material is a synthetic polymer.

16. A composition of claim 15, wherein said synthetic polymer is a polyolefin homopolymer or copolymer.

17. A composition of claim 15, wherein said synthetic polymer is a styrene homopolymer, copolymer or terpolymer.

* * * * *